US007172613B2

(12) United States Patent
Wazne

(10) Patent No.: US 7,172,613 B2
(45) Date of Patent: Feb. 6, 2007

(54) INTRAGASTRIC DEVICE FOR TREATING MORBID OBESITY

(75) Inventor: Hussein Wazne, Saint-Bardoux (FR)

(73) Assignee: Districlass Medical SA, Saint-Etienne (FR)

( * ) Notice: Subject to any disclaimer, the term of this patent is extended or adjusted under 35 U.S.C. 154(b) by 679 days.

(21) Appl. No.: 10/221,562

(22) PCT Filed: Mar. 2, 2001

(86) PCT No.: PCT/FR01/00627

§ 371 (c)(1),
(2), (4) Date: Feb. 21, 2003

(87) PCT Pub. No.: WO01/68007

PCT Pub. Date: Sep. 20, 2001

(65) Prior Publication Data
US 2003/0158569 A1   Aug. 21, 2003

(30) Foreign Application Priority Data
Mar. 13, 2000 (FR) .................................. 00 03161

(51) Int. Cl.
A61M 29/00 (2006.01)
(52) U.S. Cl. ...................................................... 606/192

(58) Field of Classification Search ................ 606/151, 606/153, 157, 191, 192, 194; 604/96.01, 604/97.01, 97.02, 99.01
See application file for complete search history.

(56) References Cited

U.S. PATENT DOCUMENTS

| 4,246,893 | A | 1/1981 | Berson |
| 5,084,061 | A | 1/1992 | Gau et al. |
| 5,234,454 | A | 8/1993 | Bangs |
| 5,259,399 | A | 11/1993 | Brown |
| 6,454,785 | B2 * | 9/2002 | De Hoyos Garza ......... 606/192 |

FOREIGN PATENT DOCUMENTS

WO   99/25418   5/1999

* cited by examiner

Primary Examiner—Kevin Truong
(74) Attorney, Agent, or Firm—Young & Thompson

(57) ABSTRACT

An intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume.

15 Claims, 5 Drawing Sheets

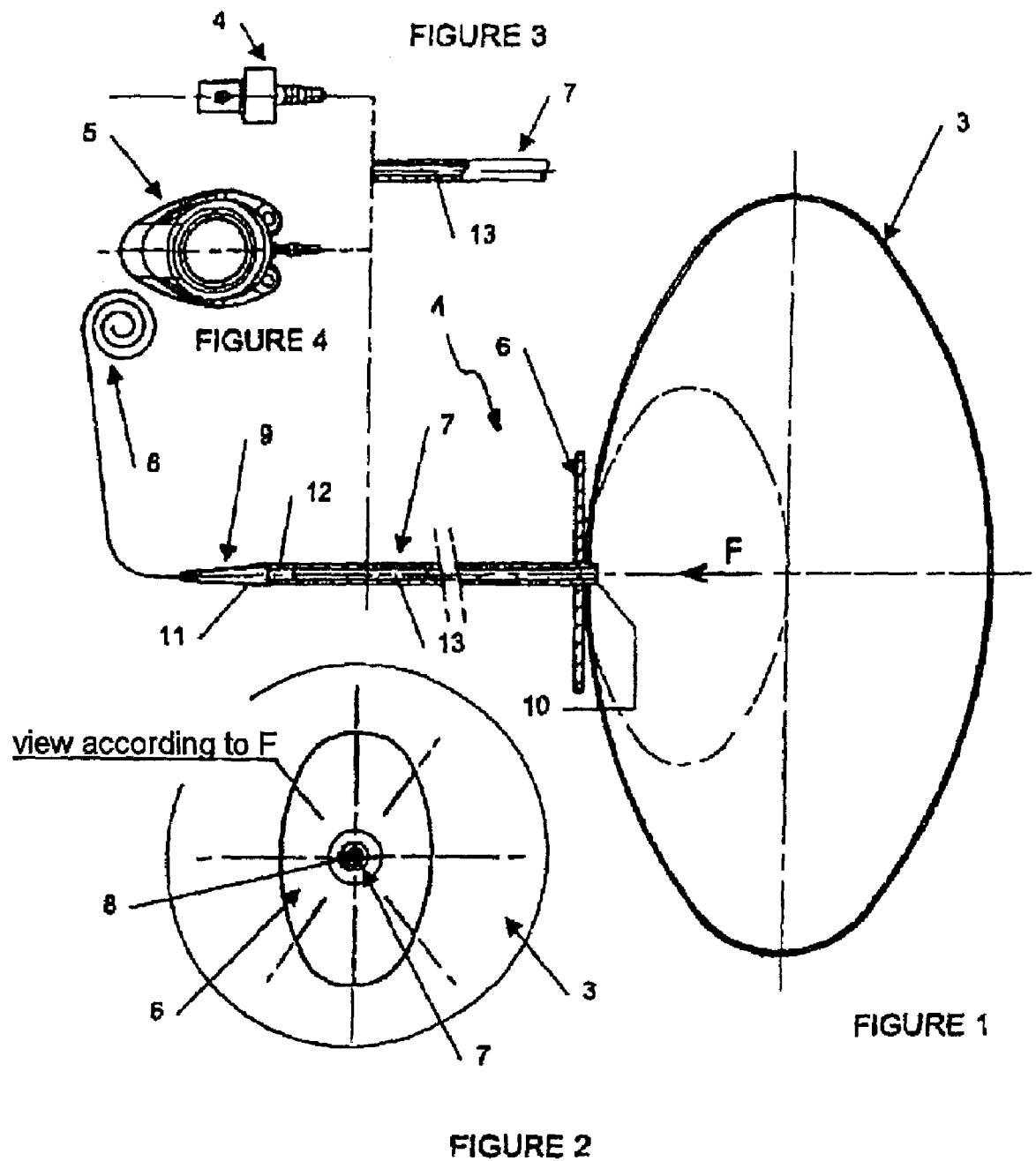

INTRAGASTRIC DEVICE FOR TREATING MORBID OBESITY

BACKGROUND OF THE INVENTION

The present invention relates to an intragastric device which is introduced by an endoscopy procedure and permits treatment of patients suffering from morbid obesity.

Devices for treatment of morbid obesity are known which consist of a ring which is positioned surgically around the cardiac part of the stomach in order to limit the amount of food absorbed.

The positioning of this type of device involves surgical operations which impose a burden on the patient.

In addition, this device has certain disadvantages because many problems or surgical complications arise after the use of this treatment technique.

The U.S. Pat. No. 5,259,399 has disclosed a device with an elastic balloon which is introduced into the stomach from the outside by way of a permanent trocar fixed on the patient so as to empty into the stomach.

The device with an elastic balloon of variable volume comprises means for rendering it leaktight and fixing it on the trocar in order to prevent any external escape from the stomach.

It is noted that this device has certain disadvantages as regards its effectiveness in the treatment of morbid obesity.

The use of a rigid trocar is a major handicap for the patient because it prevents movements of various tissues and muscles, resulting in pain or discomfort for the patient.

In addition, the elastic balloon of variable volume can be inflated until occlusion of the patient's stomach, which entails a major risk.

The balloon of variable volume, on account of its elasticity, and when it is not inflated to its maximum volume, is not able to oppose the volume of food ingested.

This is because the passage of the food leads to a deformation of the elastic balloon.

SUMMARY OF THE INVENTION

The intragastric device according to the present invention is easily introduced by an endoscopy procedure which can be performed under local or general anesthesia by gastroenterologists or surgeons.

Thus, the intragastric device according to the present invention is made up of a set of devices each comprising a balloon or envelope of defined nominal volume.

Thus, the object of the intragastric device according to the invention is to fill a volume by way of a balloon of defined nominal volume which is inflated inside the stomach.

With the intragastric device according to the present invention, it is possible to reduce the volume of the stomach, and hence the amount ingested to give the patient a feeling of fullness, without any of the psychological or physiological trauma associated with a strict diet.

Moreover, the balloon of the intragastric device according to the present invention is retained against the inner wall of the stomach, affording the patient comfort and avoiding possible migrations or blocking of the digestive tract.

The intragastric device according to the present invention, introduced by an endoscopy procedure into the stomach of a patient for treating morbid obesity, is made up of a set of devices each comprising a balloon or envelope of defined nominal volume which is connected in a leaktight manner to connection means consisting of a disk forming a support base for the balloon against the inner wall of the stomach, a flexible tube or catheter for connecting the balloon to a supply device, and securing means integral with the tube or catheter, said connection means making it possible, on the one hand, to position and/or recover the balloon and, on the other hand, to fix the supply device either outside the patient's body or subcutaneously, in order to be able to bring the balloon or envelope to its defined nominal volume.

The intragastric device according to the present invention comprises a disk which is positioned about the flexible tube or catheter and against the outer wall of the balloon or envelope.

The intragastric device according to the present invention comprises a balloon which is fixed about the tube or catheter so that the latter opens out inside said balloon.

The intragastric device according to the present invention comprises securing means which consist of a joining piece of conical profile integral with a filament.

The intragastric device according to the present invention comprises a joining piece having a stub which penetrates inside an internal bore of the tube or catheter.

The intragastric device according to the present invention comprises a filament having a straight or looped profile.

The intragastric device according to the present invention comprises a disk which is of circular shape.

The intragastric device according to the present invention comprises a disk which is of oval shape.

The intragastric device according to the present invention comprises a balloon or envelope which has an oval profile or other profile which is symmetrical with respect to the horizontal axis of the tube or catheter.

The intragastric device according to the present invention comprises a balloon or envelope which has an oval profile or other profile which is asymmetrical with respect to the horizontal axis of the tube or catheter.

The intragastric device according to the present invention comprises a balloon or envelope which has a kidney-bean-shaped profile symmetrical with respect to the horizontal axis of the tube or catheter.

The intragastric device according to the present invention comprises a balloon or envelope which has a kidney-bean-shaped profile asymmetrical with respect to the horizontal axis of the tube or catheter.

BRIEF DESCRIPTION OF THE DRAWINGS

The following description in which reference is made to the attached drawings, which are given as nonlimiting examples, will permit a better understanding of the invention, its characteristics, and its advantages.

FIG. 1 is a view illustrating the intragastric device according to the present invention.

FIG. 2 is a view according to F in FIG. 1, showing the shape of the disk supporting the intragastric device according to the present invention.

FIG. 3 is a view showing a supply device of the nonreturn valve type which is fixed on the flexible tube or catheter of the intragastric device according to the present invention.

FIG. 4 is a view showing another feed device of the implantable chamber type which is fixed on the flexible tube or catheter of the intragastric device according to the present invention.

DETAILED DESCRIPTION OF THE PREFERRED EMBODIMENTS

Figure 5:
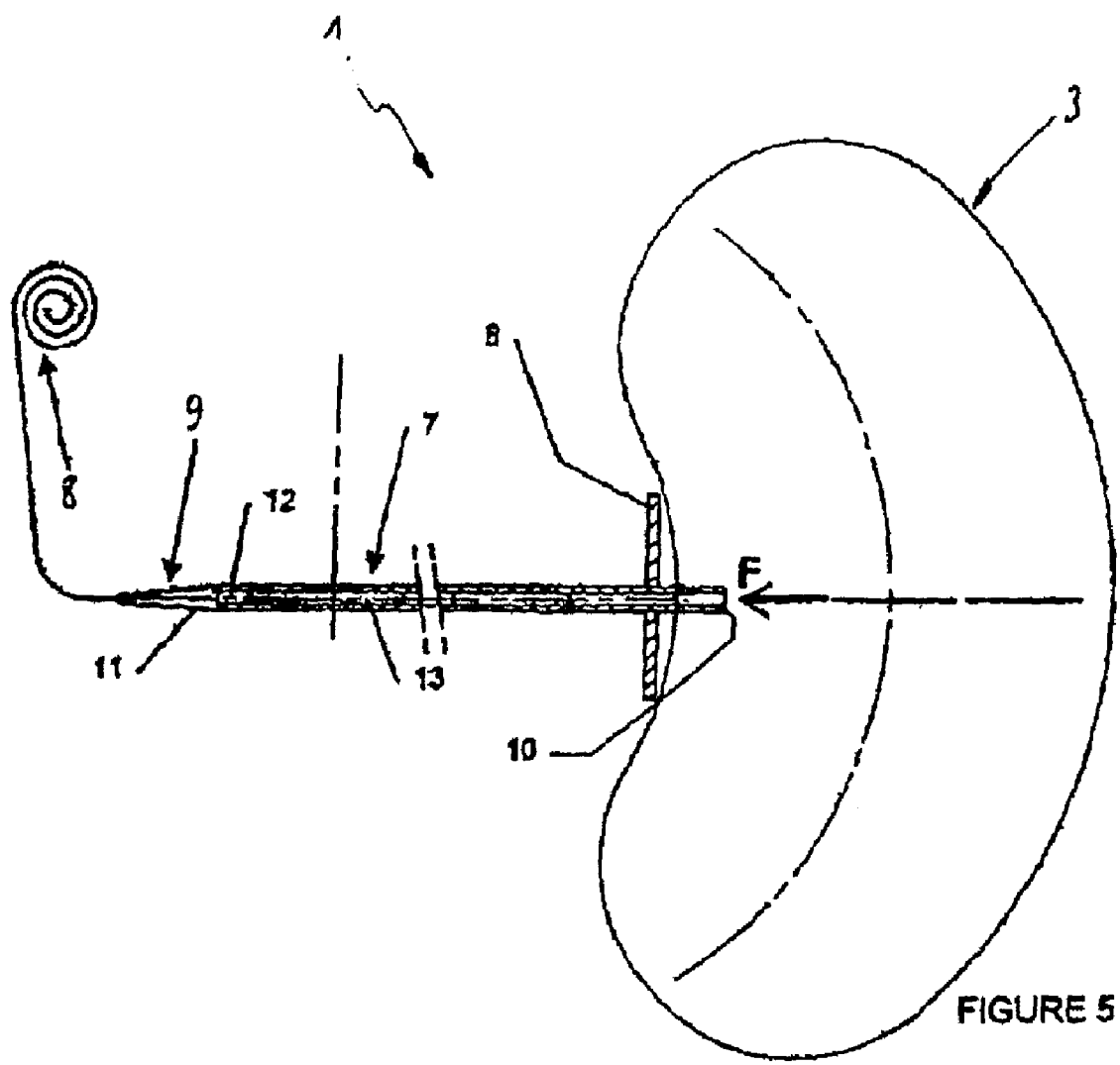
FIG. 5 is a view showing a variant of the balloon or envelope of the intragastric device according to the present invention.

In FIGS. 1 and 2, an intragastric device 1 has been shown which is implanted in the stomach 2 of a patient, and of which the shape and nominal volume of a balloon or envelope 3 is defined and permits the treatment of a patient suffering from morbid obesity.

Each intragastric device is made up of a set of devices each comprising a balloon or envelope 3 of defined nominal volume of between 100 cubic centimeters and 1100 cubic centimeters.

The intragastric device 1 comprises a balloon or envelope 3 of oval or other shape whose defined nominal volume is obtained by the quantity of liquid or gas injected into it.

The intragastric device 1 comprises connection means making it possible, on the one hand, to position and/or recover the balloon or envelope 3 and, on the other hand, to fix a supply device 4, 5 either outside the patient's body or subcutaneously, in order to be able to bring the balloon or envelope 3 to its defined nominal volume.

The connection means consist of a disk 6 forming a support base for the balloon or envelope 3 against the inner wall of the stomach 2, and of a hollow tube or catheter 7 which is flexible for connection to a supply device 4, 5.

The balloon or envelope 3 has an oval profile or other profile which is symmetrical with respect to the horizontal axis of the flexible tube or catheter 7.

In one variant, the balloon or envelope 3 can have an oval profile or other profile which is asymmetrical with respect to the horizontal axis of the flexible tube or catheter 7.

The tube or catheter 7 comprises securing means 9 which are arranged at the opposite end from the disk 6.

The disk 6 and the tube or catheter 7 are made from the same plastic material such as polyurethane or silicone or the like.

In a nonlimiting manner, the disk 6 has either a circular shape or an oval shape extending perpendicular about the outer periphery of the tube or catheter 7.

The disk 6 is positioned about the tube or catheter 7 in such a way as to define a cylindrical bearing surface 10 of small dimension constituting a support on the inner wall of the stomach.

The disk 6 is positioned about the flexible tube or catheter 7 and against the outer wall of the balloon or envelope 3.

The disk 6 is designed in such a way as to be able to undergo elastic deformation so as to press flat against the inner wall of the stomach 2 during introduction of the intragastric device 1.

The securing means 9 consist of a joining piece 11 of conical profile integral with a stub 12 which penetrates inside the internal bore 13 of the flexible tube or catheter 7.

The conical profile of the joining piece 11 is intended to facilitate the dilation of the tissues, in order to withdraw the tube or catheter 7 outside the stomach 2 and the abdominal wall.

In the continuation of its conical profile, the joining piece 11 is integral with a filament 8 which can be straight or looped.

In FIG. 5, the intragastric device 1 according to the present invention has been shown comprising a balloon or envelope 3 whose outer shape has a kidney-bean profile which is symmetrical with respect to the horizontal axis of the flexible tube or catheter 7.

This particular profile of the balloon or envelope 3 permits, when the latter is brought to its defined nominal volume, a better adaptation to the inner contour of the patient's stomach 2.

Figure 6:
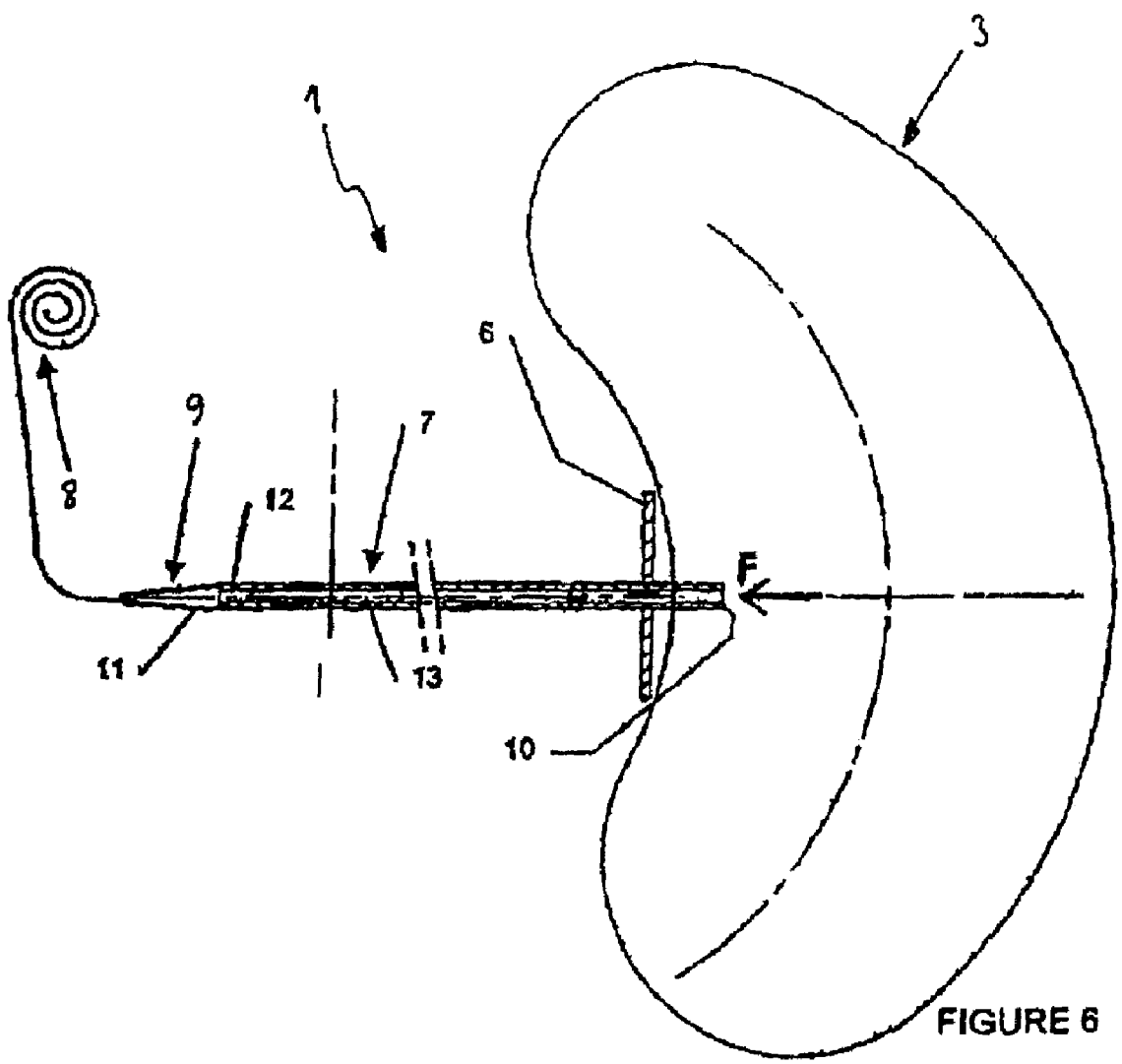
FIG. 6 is a view showing another variant of the balloon or envelope of the intragastric device according to the present invention.

In FIG. 6, the intragastric device 1 according to the present invention has been shown in which the balloon or envelope 3 has a kidney-bean-shaped outer profile which is asymmetrical with respect to the horizontal axis of the flexible tube or catheter 7.

Specifically, it will be noted that the balloon or envelope 3 of kidney-bean shape has, above the horizontal axis of the tube or catheter 7, a part whose volume is greater than the part situated below said tube or catheter.

The asymmetrical profile of the balloon or envelope 3 in relation to the horizontal axis of the tube or catheter 7 allows the latter to adapt to the inner profile of the stomach 2.

Figure 7:
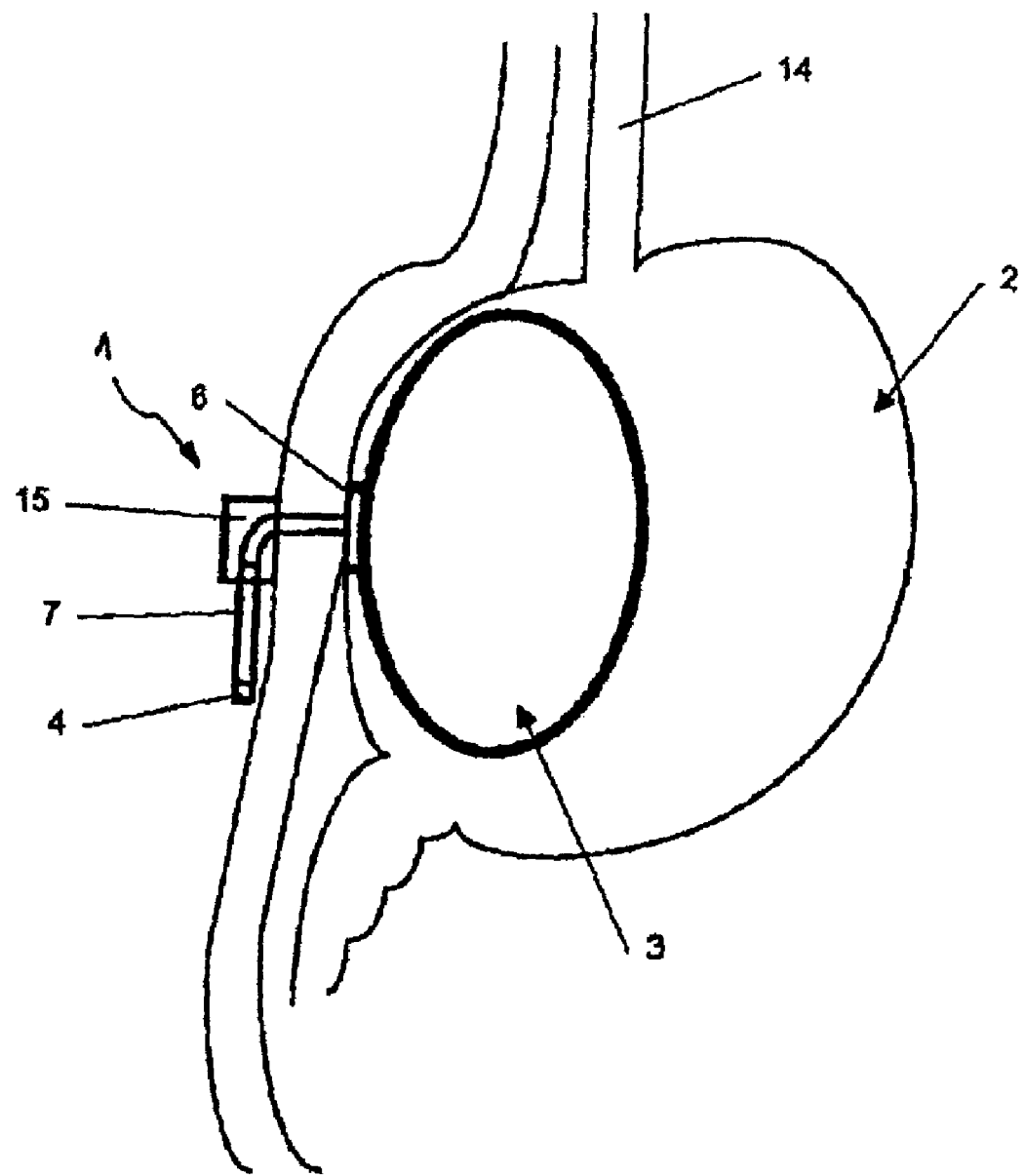
FIG. 7 is a diagrammatic view illustrating the positioning, on the patient, of the intragastric device integral with the feed device of the nonreturn valve type.

In FIG. 7, the intragastric device 1 has been shown inside the stomach 2 of a patient. This device is put in place by an endoscopy procedure, passing it through the mouth and then the esophagus 14 and positioning it in the stomach 2.

The operating surgeon proceeds to recover the tube or catheter 7 percutaneously by virtue of the securing means 9 with which it is possible to spread the tissues apart without tearing them.

The tube or catheter 7 is fixed by an attachment system 15 to the skin of the patient's belly in order to hold the intragastric device 1 in place.

The tube or catheter 7 is then cut outside the patient's body to remove the joining piece 11 integral with the filament 8 constituting the securing means 9, and to permit fitting of a supply device 4 with nonreturn valve.

The balloon or envelope 3 is inflated by way of a syringe or the like (not shown) which is fitted onto the supply device 4 in order to bring said balloon or envelope to its defined nominal volume.

Once the defined nominal volume of the balloon 3 is reached, the latter is pressed flat against the inner wall of the stomach 2, by means of external traction on the tube or catheter 7, so as to ensure, by virtue of the disk 6, perfect leaktightness between the stomach 2 and the peritoneal cavity.

Figure 8:
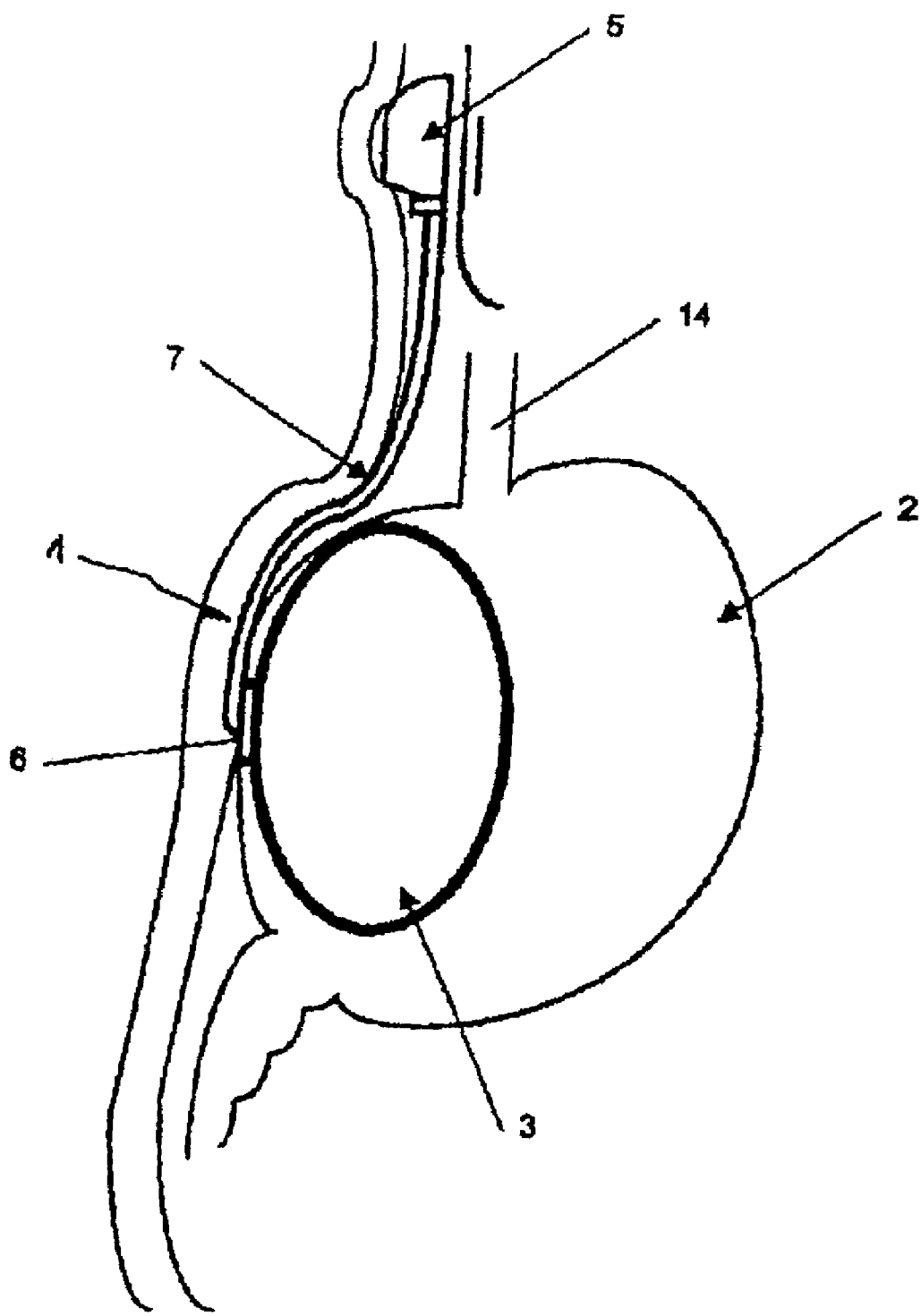
FIG. 8 is a diagrammatic view showing the positioning, on the patient, of the intragastric device integral with the feed device of the implantable chamber type.

In FIG. 8, the intragastric device 1 has been shown inside the stomach 2 of a patient. This device is put in place by an endoscopy procedure, passing it through the mouth and then the esophagus 14 and positioning it in the stomach 2.

The operating surgeon proceeds to recover the tube or catheter 7 percutaneously by virtue of the securing means 9 with which it is possible to spread the tissues apart without tearing them.

The tube or catheter 7 is fixed by an aponeurotic attachment system which holds the intragastric device 1 in place.

The tube or catheter 7 is then cut to remove the joining piece 11 integral with the filament 8, in order to permit the fitting of a supply device of the implantable chamber type 5 which is positioned subcutaneously.

The balloon or envelope 3 is brought to its defined nominal volume by way of a Huber needle associated with a syringe (not shown) which is introduced into the implantable chamber 5, available on the market, for example, under the name "Districath".

Once the defined nominal volume of the balloon or envelope 3 is reached, the latter is pressed flat against the inner wall of the stomach 2, by means of external traction on the tube or catheter 7, so as to ensure, by virtue of the disk 6, perfect leaktightness between the stomach 2 and the peritoneal cavity.

It will be noted that the effect of the intragastric device 1 is to reduce the volume of the stomach 2 and hence the amount ingested to give the patient a feeling of fullness.

It will be noted that the intragastric device 1 does not require any surgical intervention imposing a burden on the patient and causing trauma.

It will be noted that the intragastric device 1 can be easily removed at the end of treatment on account of its external or subcutaneous fixation.

It will be noted that the defined nominal volume of each balloon or envelope 3 of a set of intragastric devices 1 will never obstruct the maximum volume of the stomach, so as to avoid any occlusion of the latter and thereby safeguard the patient.

It must also be understood that the above description has been given only by way of example and that it does not in any way limit the scope of the invention, and that the details described could be replaced by any other equivalent means without thereby departing from said scope of the invention.

The invention claimed is:

1. An intragastric device introduced by an endoscopy procedure into the stomach of a patient for treating morbid obesity, comprising:
    a balloon of defined nominal volume; and
    connection means which is connected to said balloon in a leaktight manner,
    said connection means consisting of a disk forming a support base for the balloon against an inner wall of a patient's stomach, a flexible tube or for connecting the balloon to a supply device, and securing means integral with the tube,
    said connection means making it possible to at least one of position and recover the balloon and, to fix the supply device either outside the patient's body or subcutaneously, in order to be able to bring the balloon to the defined nominal volume.

2. The intragastric device as claimed in claim 1, wherein the disk is positioned about the tube and against an outer wall of the balloon.

3. The intragastric device as claimed in claim 2, wherein the balloon is fixed about the tube so that the tube opens out inside said balloon.

4. The intragastric device as claimed in claim 1, wherein the securing means consist of a joining piece of conical profile integral with a filament.

5. The intragastric device as claimed in claim 4, wherein the joining piece has a stub which penetrates inside an internal bore of the tube.

6. The intragastric device as claimed in claim 4, wherein the filament has a straight or looped profile.

7. The intragastric device as claimed in claim 1, wherein the disk is of circular shape.

8. The intragastric device as claimed in claim 1, wherein the disk is of oval shape.

9. The intragastric device as claimed in claim 1, wherein the balloon has a profile which is symmetrical with respect to a horizontal axis of the tube.

10. The intragastric device as claimed in claim 1, wherein the balloon has a profile which is asymmetrical with respect to a horizontal axis of the tube.

11. The intragastric device as claimed in claim 1, wherein the balloon has a kidney-bean-shaped profile symmetrical with respect to a horizontal axis of the tube.

12. The intragastric device as claimed in claim 1, wherein the balloon has a kidney-bean-shaped profile asymmetrical with respect to the horizontal axis of the tube.

13. An intragastric device introduced by an endoscopy procedure into a stomach of a patient for treating morbid obesity, comprising:
    an inflatable envelope having a defined nominal volume;
    means for connecting said inflatable envelope against an inner wall of a patient's stomach in a leaktight manner;
    a flexible tube for connecting said inflatable envelope to a supply device; and
    means for securing the intragastric device to a patient, said means for securing being integral with said tube.

14. An intragastric device introduced by an endoscopy procedure into a stomach of a patient for treating morbid obesity, comprising:
    a balloon of defined nominal volume;
    a flexible catheter connecting said balloon to a supply device;
    a disk directly connected to said flexible catheter and supporting said balloon against an inner wall of a patient's stomach and being connected to said balloon so that said disk and balloon together form a leaktight seal; and
    a securing member integral with said catheter,
    wherein said disk enables a doctor to at least one of position and recover the balloon and, to fix the supply device either outside a patient's body or subcutaneously.

15. The intragastric device as claimed in claim 14, wherein the disk is positioned against an outer wall of the balloon.

* * * * *